United States Patent
Birks et al.

(10) Patent No.: US 9,423,340 B2
(45) Date of Patent: Aug. 23, 2016

(54) AQUEOUS OZONE MONITOR UTILIZING GAS STRIPPING

(71) Applicant: 2B Technologies, Inc., Boulder, CO (US)

(72) Inventors: John W. Birks, Boulder, CO (US); Bova Xiong, Erie, CO (US); Christopher M. Ford, Denver, CO (US); Peter C. Andersen, Boulder, CO (US); Craig J. Williford, Boulder, CO (US)

(73) Assignee: 2B Technologies, Inc., Boulder, CO (US)

( * ) Notice: Subject to any disclaimer, the term of this patent is extended or adjusted under 35 U.S.C. 154(b) by 0 days.

(21) Appl. No.: 14/752,149

(22) Filed: Jun. 26, 2015

(65) Prior Publication Data
US 2015/0377772 A1     Dec. 31, 2015

Related U.S. Application Data

(60) Provisional application No. 62/018,405, filed on Jun. 27, 2014.

(51) Int. Cl.
   *G01N 21/00*     (2006.01)
   *G01N 21/33*     (2006.01)
   (Continued)

(52) U.S. Cl.
   CPC .............. *G01N 21/33* (2013.01); *C02F 1/78* (2013.01); *G01N 33/18* (2013.01); *C02F 2209/23* (2013.01); *C02F 2209/235* (2013.01);
   (Continued)

(58) Field of Classification Search
CPC ...... A62D 3/38; C12N 1/26; G01N 35/1097; G01N 21/3151; G01N 2021/3181; B01J 2208/00955; A61L 2/202; B01D 2257/90

USPC .......................................... 356/437; 436/116
See application file for complete search history.

(56) References Cited

U.S. PATENT DOCUMENTS

| | | | |
|---|---|---|---|
| 7,502,114 B2 * | 3/2009 | Levine ............... | G01N 21/3151 356/432 |
| 2003/0194692 A1 * | 10/2003 | Purdum ................. | C12N 13/00 435/2 |

(Continued)

OTHER PUBLICATIONS

Wilson, Kevin L., and John W. Birks, "Mechanism and Elimination of a Water Vapor Interference in the Measurement of Ozone by UV Absorbance", Environmental Science & Technology, vol. 40, No. 20, 2006. 7 pages.

(Continued)

*Primary Examiner* — Tarifur Chowdhury
*Assistant Examiner* — Isiaka Akanbi (57) ABSTRACT

The present invention provides a means of measuring the concentration of ozone dissolved in water or another solvent. Small, discrete samples are sparged with air or another unreactive gas for a short period of time to measure a profile of ozone vs time in the sparge gas. The total amount of ozone in the original sample is obtained by integrating under the ozone vs time profile. A correction may be made for ozone remaining in the sample after a finite sparge time by integrating under the profile tail using a decay constant obtained from the measured ozone vs time profile. The method differs from previous methods based on sparging of the sample in that a Henry's Law equilibrium or constant ratio of ozone present in the gas and liquid phases is not assumed and the flow rates of sample and sparge gas are not continuous.

13 Claims, 4 Drawing Sheets

(51) Int. Cl.
*C02F 1/78* (2006.01)
*G01N 33/18* (2006.01)
*G01N 1/00* (2006.01)
*G01N 1/40* (2006.01)

(52) U.S. Cl.
CPC ............ *C02F2303/04* (2013.01); *G01N 1/00* (2013.01); *G01N 2001/4066* (2013.01)

(56) References Cited

U.S. PATENT DOCUMENTS

| | | | | |
|---|---|---|---|---|
| 2006/0073605 | A1* | 4/2006 | Horan | G01N 31/005 436/155 |
| 2007/0095647 | A1* | 5/2007 | Dundore | A61L 2/202 204/157.15 |
| 2007/0292308 | A1* | 12/2007 | Horan | C01B 13/10 422/63 |
| 2008/0198381 | A1* | 8/2008 | Heggs | G01N 21/3504 356/437 |
| 2008/0242875 | A1* | 10/2008 | Hong | A62D 3/38 549/42 |

OTHER PUBLICATIONS

Bader, H. and J. Hoigne, "Determination of Ozone in Water by the Indigo Method", Water Research, vol. 15, pp. 449-456, 1981. 8 pages.

Bognar, John A., and John W. Birks, "Miniaturized Ultraviolet Ozonesonde for Atmospheric Measurements", Analytical Chemistry, vol. 68, No. 17, Sep. 1, 1996. 4 pages.

Majewski, Jacek, "Methods for Measuring Ozone Concentration in Ozone-Treated Water", 2012. 3 pages.

Standard Methods Committee, "4500-03 (Residual)". Inorganic Nonmetals, 1997. 3 pages.

* cited by examiner

AQUEOUS OZONE MONITOR UTILIZING GAS STRIPPING

BACKGROUND

Due to its high oxidation potential, bactericidal properties, ease of on-site generation from air or oxygen, and ease of destruction to form ordinary oxygen, ozone has become widely used in a large number of applications such as water treatment, food processing, odor removal, aquaculture and soil and ground water remediation. In most applications ozone, produced in an electrical discharge of air or oxygen, is dissolved in water, usually under high pressure. As examples, the water treated can be municipal drinking water, bottled water, water to be used in beverages, wastewater, water used in aquaculture and contaminated ground water. Ozonated water also is widely used as a bactericidal rinse for meats and vegetables being processed for food and as a cleaning agent for semiconductor chips and other electronic parts. In these and many other applications, it is important to know the concentration of dissolved ozone throughout the process. The ozone concentration integrated over time represents a dose to the water being treated, the change in ozone concentration over time is often indicative of the original concentrations of contaminants in the water, and the residual concentration is important for knowing when the treatment process is complete and the water can be safely used. Thus, there are many applications requiring the measurement of dissolved ozone in water. In many cases the water being treated with ozone is not of high purity and may contain dissolved organic, inorganic and biological compounds and particulate matter. The presence of such materials makes measurement of dissolved ozone challenging in all but high purity water. In some applications, such as the semiconductor industry, ozone may be dissolved into water containing strong acids and other oxidants such as hydrogen peroxide.

Ozone in impure or "dirty" water has been measured by both batch and automated methods. Methods for measuring dissolved ozone were reviewed recently by Majewski (2012). A colorimetric method based on bleaching of the indigo dye has long been used in a batch mode (e.g., Bader and Hoigne, 1981) and is the basis of Standard Method 4500-O3 (Standard Methods Committee, 1997). Although considered accurate, this method is cumbersome, requiring hand mixing of individual water samples with a reagent solution followed by measurement of the decrease in absorbance at ~600 nm using a colorimeter. The method is often used as a calibration method for automated instruments.

Absorption of UV light has long been used as an automated method for measurements of gas-phase ozone (e.g., Bognar and Birks, 1996; Wilson and Birks, 2006) and of ozone dissolved in pure solvents with high precision and accuracy. The ozone molecule has an absorption maximum at 254 nm, coincident with the principal emission wavelength of a low-pressure mercury lamp. There are commercial instruments available for the direct measurement of ozone in high purity water and other solvents, but those instruments cannot be used for measuring ozone in drinking water and other "dirty" water because of the presence of UV-absorbing compounds and/or particles that both absorb and scatter UV radiation. In addition, the concentrations of those interfering species often change upon exposure to ozone due to chemical reactions, further complicating direct UV absorbance measurements of dissolved ozone.

At present, dissolved ozone is most commonly measured using sensors separated from the sample water by an ozone-selective membrane. The membrane allows ozone to diffuse to the sensor while minimizing the diffusion of interfering compounds. Two types of sensors are typically used in membrane-based ozone monitors, amperometric and polarographic sensors. In amperometric sensors, ozone participates in an electrochemical reaction, and the resulting electrical current is measured. These sensors have the disadvantage of producing a response to other oxidizers in the sample as well. Polarographic sensors, which vary the potential applied to an electrode, are more selective for ozone, because different species are detected as the applied potential is scanned. Although widely used, the membranes of such sensors are easily fouled and require routine maintenance.

Gas phase sensors and detectors also are used that employ a gas stripping or sparging process instead of a membrane. A stream of inert gas or ozone-free air is bubbled through the sample, or a liquid sample is sprayed into a stream of air or inert gas, and a fraction of the dissolved ozone is transferred to the gas-phase in a way that establishes an approximate equilibrium between dissolved and gas-phase ozone. The ozone concentration is then measured in the gas phase using a UV photometer or other device such as a heated metal oxide semiconductor (HMOS) ozone sensor. In theory, the gas-phase concentration is related back to the dissolved ozone concentration using Henry's Law, which states that the dissolved concentration of ozone (c) is proportional to the partial pressure (p) of ozone in the air over the surface of the water (p), $$c = p/H \quad (1)$$

where H is the Henry's constant. In order to convert ozone concentration in the gas phase to partial pressure the values of temperature of pressure of the gas also are required. Ozone has a low solubility in water and thus a high Henry's Law constant. However, Henry's Law only applies if equilibrium is established between the gas and liquid phases. Since the gas stripping process does not always achieve a perfect equilibrium, the assumption of a Henry's Law relationship can cause a significant error in the ozone measurement. The commercially available instruments based on this approach use continuous flows of both water and sparging gas, and the instruments are calibrated using the indigo blue or other method to correct for deviations from the Henry's Law equilibrium. However, the Henry's Law constant is strongly affected by the ionic strength, temperature and pH of the water, which adds additional uncertainty to the ozone measurement, especially in impure water.

Sparging (bubbling or stripping) of ozone from solution followed by measurement of ozone in the gas phase has the advantage of measuring the dissolved ozone in the absence of UV-absorbing interferences that remain in the water. However, instruments designed around this principle in the past have incorporated very large and cumbersome sparging chambers and rely on a fixed value of the Henry's Law constant that partitions ozone between the liquid and gas phases. An important way in which the invention described here differs from previously known methods for measuring dissolved ozone based on sparging is that it does not rely on establishment of an equilibrium between ozone in the gas and liquid phases and thus does not depend on the value of the Henry's Law constant, which varies with ionic strength, temperature and pH.

BRIEF SUMMARY

One aspect of the present disclosure is the measurement of ozone in dirty water; i.e., water containing dissolved inorganic and organic compounds and suspended biological materials and particulate matter that would normally interfere in the measurement of ozone.

Another aspect of this invention is the substantially large (60% to 100%) removal of ozone from a small sample of water in a gas stripping process and measurement of that ozone in the gas phase free from the aforementioned interferences present in dirty water.

Another aspect of the present invention is numerical integration under the measured ozone vs time profile to obtain a measure of the total amount of dissolved ozone sparged from a small (typically ≤2 mL) water sample. The ozone concentration in the original water sample is calculated from the total mass of ozone removed from the water divided by the mass of the water sample and multiplied by a calibration factor.

Another aspect of the present invention is a method to estimate the amount of ozone remaining in the sparged water sample after a given period of time using the measured ozone vs time profile so that a more accurate estimate may be made of the total ozone dissolved in the original sample.

Another aspect of the present invention is the ability to measure the dissolved ozone concentration in a short period of time, typically 10 seconds or less.

Another aspect of the present invention is a complete lack of reliance on Henry's Law for determining the partitioning of ozone between the solvent and gas phases, thus eliminating the reliance of the method on the establishment of an equilibrium and eliminating errors due to variations in the Henry's Law equilibrium constant due to variations in temperature, ionic strength, pH, etc.

The following embodiments and aspects thereof are described and illustrated in conjunction with systems, tools and methods which are meant to be exemplary and illustrative, not limiting in scope. In various embodiments, one or more of the above described problems have been reduced or eliminated, while other embodiments are directed to other improvements.

Disclosed herein is a method for the semi-continuous measurement of ozone dissolved in water or other solvents involving sparging of small, discrete samples of the solvent and measurement of the ozone gas stripped from the solvent and into the gas phase during the stripping process. Although the present invention uses the sparging method to remove ozone from water or another solvent, instead of relying on establishment of an equilibrium or constant partitioning of ozone between the gas and solvent, small discrete samples of the water are sparged over a short period of time (3 to 10 seconds with 5 seconds being typical) in order to remove a substantially large fraction of ozone from the sample, and the ozone concentration in the gas stream is measured as a function of time throughout the gas stripping process.

Ideally, the water sample would be exhaustively stripped with sparging gas such that the sum of ozone molecules passing through a gas-phase detector is equal to the total ozone molecules in the water sample being sparged. However, since the ozone-stripping process follows exponential decay, it is not practical to remove all of the ozone. Typically, 75-85% of the ozone is removed in 5 seconds under the conditions employed in the present embodiment. The ozone remaining in the sample can be accurately estimated by assuming that the sparging process is described by exponential decay of the dissolved ozone concentration. Thus, by measuring the ozone concentration vs time profile, one is able to obtain an accurate measure of the total ozone molecules and therefore the weight of ozone in the original sample. By dividing that weight of ozone by the weight of the water sample (typically ≤2 g), one can obtain the fractional weight of ozone in the original sample. The entire process can be repeated, approximately once every 10 seconds, to provide a relatively fast measurement of dissolved ozone in water or other solvents. The method is unaffected by variations in the Henry's Law constant due to variations in temperature, ionic strength, pH, etc.

In addition to the exemplary aspects and embodiments described above, further aspects and embodiments will become apparent by reference to the accompanying drawings forming a part of this specification wherein like reference characters designate corresponding parts in the several views.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Before explaining the disclosed embodiment of the present invention in detail, it is to be understood that the invention is not limited in its application to the details of the particular arrangement shown, since the invention is capable of other embodiments. Exemplary embodiments are illustrated in referenced figures. It is intended that the embodiments and figures disclosed herein are to be considered illustrative rather than limiting. Also, the terminology used herein is for the purpose of description and not of limitation.

DETAILED DESCRIPTION

Figure 1:
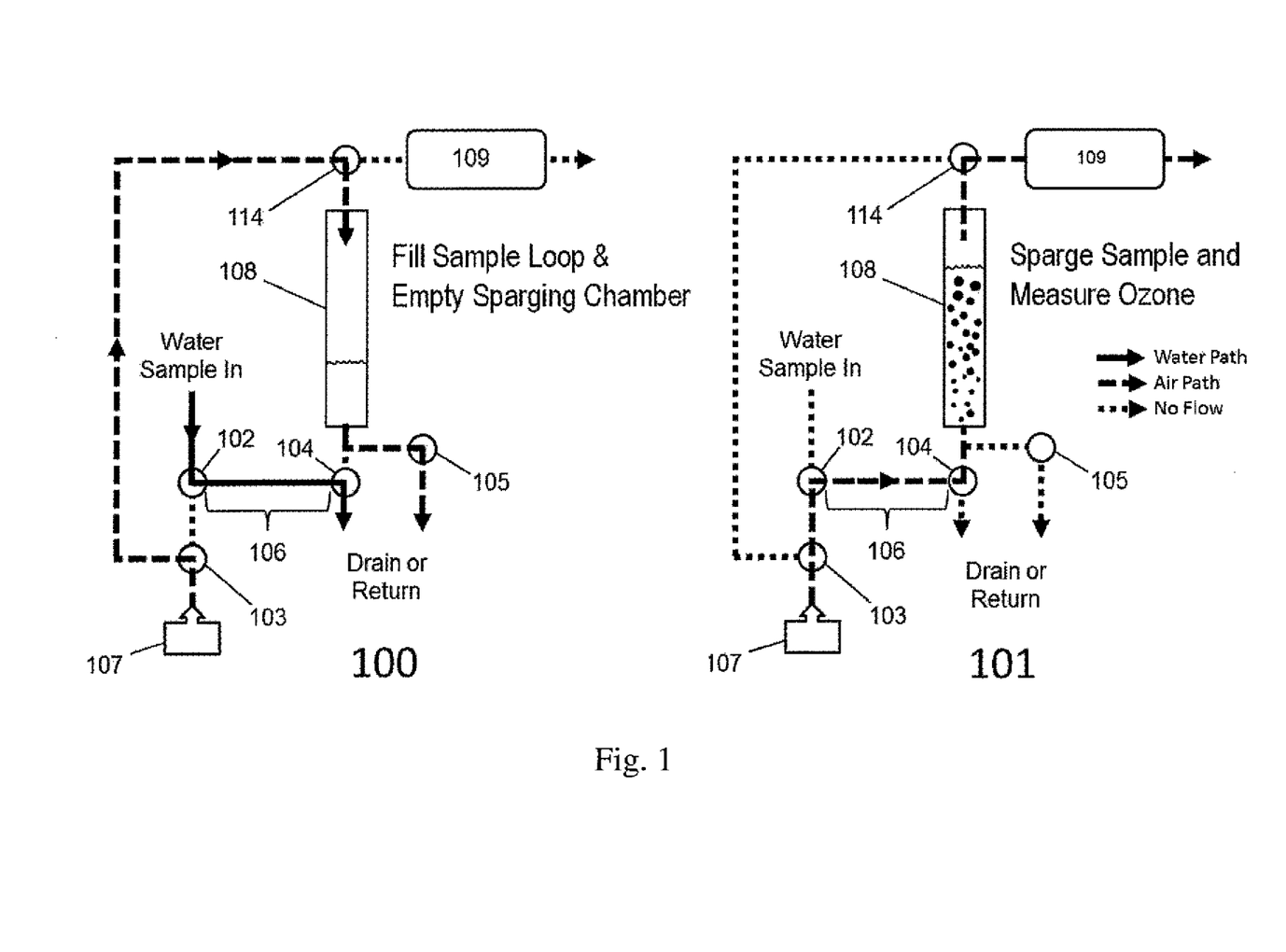
FIG. 1 is a simplified diagram of one embodiment of an aqueous ozone monitor illustrating two steps involved in sampling the water and making the measurement.

FIG. 1 is a simplified diagram of one embodiment of an aqueous ozone monitor of the present disclosure, illustrating the two steps involved in sampling the water and making the measurement. Four 2-way valves 102, 103, 104, 114 and one 1-way valve 105 direct the flow of air and water through the apparatus. The process of measuring dissolved ozone consists of two steps. In the first step (left panel of FIG. 1), the sample loop 106 is overfilled with a flow of pressurized water from the water source to be analyzed, and simultaneously an internal air pump 107 pressurizes the impinger 108 to empty ozone-depleted water from the previous sample. The volume of the sample loop is ~2 mL in this embodiment but could be smaller or larger (typically 0.5 to 10 mL), depending on the sensitivity of the ozone detector and response time desired. The only requirement of the pressure of the water source is that it be adequate to produce a flow rate that will overfill the sample loop within the time allocated for this step, which typically is 3 to 10 seconds. In the present embodiment, a pressure of 1 psi was adequate to overfill the sample loop within the 5 seconds allocated for this step. An upper limit of 50 psi was imposed by the pressure rating of the solenoid valves used in this embodiment. In the second step, valve states are changed so that air from air pump 107 both forces the water sample into the impinger 108 and sparges the sample, with the ozone-enriched air passing through the optical bench 109 where ozone is measured. The air flow rate used for transporting and sparging the sample is typically in the range 1.5 to 2.5 L/min for this embodiment, but the air flow rate could be more or less depending on the sample volume, here ~2 mL, design and volume of the sparging chamber and flow rate requirement of the ozone detector. In the current embodiment the sparging chamber is a vertical tube having an internal diameter of 0.5 in (1.27 cm) and length of 4 in (25.4 cm) and is filled with 0.25 in (0.635 cm) PTFE beads. Many different sparging chamber designs are possible. It is desirable that the sparging chamber be easily removed for cleaning or replacement as necessary since particulate matter and non-volatile compounds and salts will be deposited within the sparging chamber. For applications involving ozone dissolved in solvents containing strong acids and/or other oxidants, as in the semiconductor industry, materials should be selected that are resistant to those chemicals. In the one embodiment, each of the two steps requires approximately 5 seconds, and a new ozone measurement is reported every 10 seconds.

Figure 2:
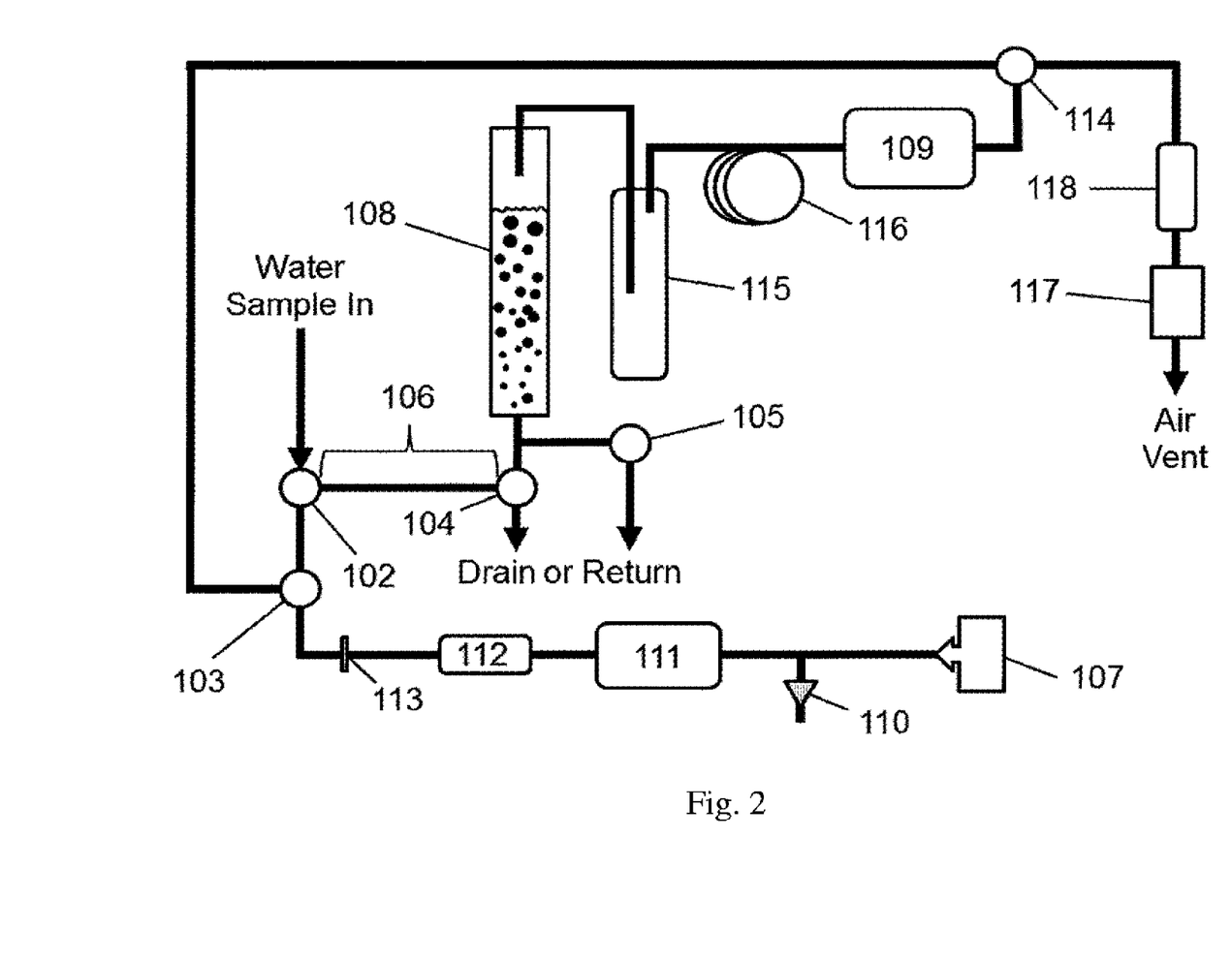
FIG. 2 is a schematic diagram of one embodiment of an aqueous ozone monitor showing additional components.

FIG. 2 is a schematic diagram of one embodiment of an aqueous ozone monitor showing additional components. Valves 102, 103, 104 and 114 are 3-way valves. Valve 105 is a 2-way valve. Sample water (or other solvent) enters at valve 102, fills the sample loop 106 and exits valve 104 where it may return to the vessel being sampled or disposed of. An air pump 107 forces air through a tee connected to bleed valve 110 which can be adjusted to control the air flow rate through the flow path, next through a pulse dampener 111, next through an ozone scrubber 112 to remove any ozone in the air, next through a particle filter 113, and next into the common port of valve 103. From valve 103, the air may vented by passing through valve 114 and then through the ozone scrubber 118 and air flow meter 117. Alternatively, air entering valve 103 is directed to pass through valve 102 and valve 104 to force the water contained in the sample loop 106 into the impinger 108 and sparge the water sample. Air departing the impinger 108 passes through a water trap 115 to capture large droplets of water, next through a Nafion® Tube 116 to equilibrate the humidity level with ambient humidity, and next through the optical bench 109 where the gas-phase ozone concentration is measured. Air passing through the optical bench 109 next passes through valve 114 followed by ozone scrubber 118 to remove ozone and then through an air flow meter 117 to measure the flow rate of the air. Air may then be vented back to the atmosphere. Note that the optical bench 109, which measures ozone by UV absorbance at 254 nm, can be replaced with any ozone measurement device such as a HMOS or electrochemical sensor.

The impinger is emptied by using valve 114 to divert air through the optical bench in the reverse direction, during which time a baseline light intensity $I_o$ is measured, next through Nafion® tube 116, water trap 115 and into to impinger 108, forcing water to drain through valve 105. At the same time the impinger 108 is being emptied, the sample loop 106 is filled with a new sample of water by forcing water through valve 102, through the sample loop 106 and out the drain 104. In this embodiment, the complete process is repeated once every 10 seconds.

Figure 3:
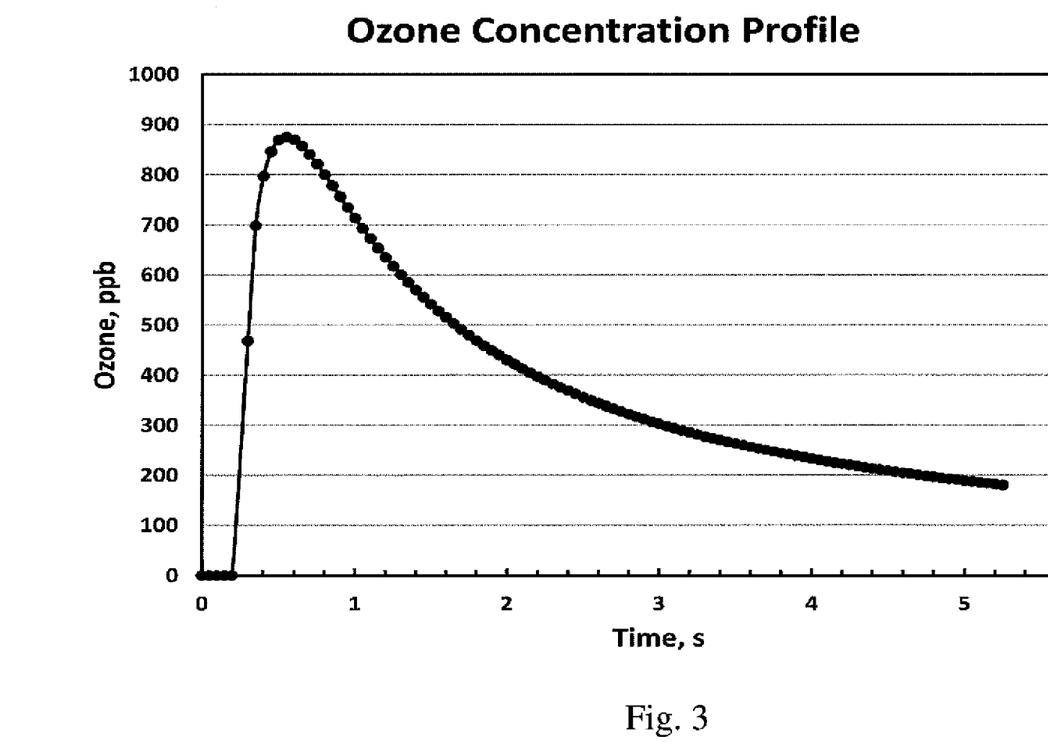
FIG. 3 shows a simulated ozone concentration vs. time profile for sparging of 2 mL of water with air.

FIG. 3 shows a simulated ozone concentration vs time profile for sparging of a water sample. For convenience the ozone units are displayed as a gas-phase mixing ratio in parts-per-billion. The simulation is based on the equation for rise-fall kinetics:

$$C = \frac{A}{k_2 - k_1}(e^{-k_2 t} - e^{-k_1 t}) \qquad (2)$$

Here, C is the concentration of ozone expressed as a mixing ratio in parts-per-billion, and the constants are chosen for illustrative purposes to be A=1,000 ppb, $k_1$=1 s$^{-1}$ and $k_2$=0.04 s$^{-1}$. This equation provides a curve that approximates the observed ozone vs time profile. The simulation shows that after five seconds of sparging some ozone still remains in solution. For this reason it is desirable to correct for the ozone in the "tail" of the ozone vs time profile.

In the gas stripping method described here, the total quantity of ozone in a small volume of ~2 mL is sparged from solution over a period of ~5 s using ozone-scrubbed ambient air, and the ozone concentration vs time profile is measured in the gas phase. During the sparging period a large fraction of the ozone is removed from solution. Integration under the ozone-time profile provides the total number of molecules of ozone (and thus the weight of ozone) in the ~2 mL sample. A small correction is made for the ozone that remains in solution based on the measured rate of exponential decay in the tail of the ozone-time profile.

In this embodiment, UV absorbance was used to measure ozone in the gas phase. However, other embodiments could make use of other gas-phase ozone detection methods such as but not limited to electrochemical or HMOS sensors. The optical bench for the UV absorbance measurement is identical to that of the 2B Technologies Model 106-M Ozone Monitor™. Ozone is measured based on the attenuation of UV light passing through a 6-cm absorption cell fitted with quartz windows. A low-pressure mercury lamp is located on one side of the absorption cell, and a photodiode is located on the opposite side of the absorption cell. The photodiode has a built-in interference filter centered on 254 nm, the principal wavelength of light emitted by the mercury lamp. Light intensity is continuously measured at a rate of 20 Hz, i.e., once every 0.05 seconds. At the beginning of the Sparge cycle (right panel of FIG. 1), ozone-free air remaining from the previous Fill and Purge cycle (left panel of FIG. 1) passes through the absorption cell, and the light intensity in the absence of ozone ($I_o$) is obtained as an average of 3 data points. The light intensity then begins to fall as ozone sparged from the solution begins to pass through the detection cell.

More than 100 measurements of the light intensity (I) are made over the period of ~5 seconds required to remove ~75-85% of the ozone from solution, and the concentration of ozone molecules is calculated for each measurement to create an ozone concentration vs. time profile using the Beer-Lambert Law, $$C_{O_3} (\text{molec/cm}^3) = 10^9 \frac{1}{\sigma l} \ln\left(\frac{I_o}{I}\right) \qquad (3)$$

where l is the path length (14 cm) and σ is the absorption cross section for ozone at 254 nm (1.15×10$^{-17}$ cm$^2$ molecule$^{-1}$ or 308 atm$^{-1}$ cm$^{-1}$). We can obtain the total number of ozone molecules in the original ~2 mL sample of water by integrating under the ozone profile curve and multiply by the volumetric flow rate, F(cm$^3$/s), $$N_{O_3} = F \int_0^\infty C_{O_3} dt \qquad (4)$$

but we can only measure ozone out to some finite time t, which is about 5 seconds in the depicted example. Thus, we separate the integral into two parts, $$N_{O_3} = F\int_0^t C_{O_3} dt + F\int_t^\infty C_{O_3} dt \qquad (5)$$

or $$N_{O_3} = N_{O_3}(\text{profile}) + N_{O_3}(\text{tail}) \qquad (6)$$

The first term is the integral under the measured profile of FIG. 2 out to a time t of ~5 s. In theory it takes an infinite time to sparge all of the ozone from solution; thus the second term is calculated based on exponential removal of ozone from solution. The exponential decay constant, k, is calculated from a fit to the last one second of measured data, and the second term, or "tail" of the ozone profile is calculated as, $$N_{O_3}(\text{tail}) = F(C_{O_3})_t \int_0^\infty e^{-kt} dt = \frac{F}{k}(C_{O_3})_t \qquad (7)$$

where $(C_{O3})_t$ is the concentration of ozone at time t (end of measurement period) and k is the exponential decay constant (units of $s^{-1}$) for removal of ozone from solution. The total number of molecules of ozone in the sparged sample is given by the sum of ozone molecules measured under the ozone profile and ozone molecules calculated to be in the tail of the decay curve. Once we know the total number of molecules in the sample loop volume V, we can calculate the dissolved ozone concentration, $$C_{O_3,aqueous}(\text{ppm}) = \frac{N_{O_3}(\text{total})}{N_A} \frac{48}{V\rho_{H_2O}} \times 10^6 \qquad (8)$$

where $N_A$ is Avagadro's number ($6.022 \times 10^{23}$ molec/mol), 48 is the molecular weight of ozone in g/mol, V is the volume of the sample loop in mL (~2 mL), and $\rho H_2O$ is the density of water (1 g/mL).

Note that dissolved ozone is expressed on a weight-weight basis and that:

$$1 \text{ ppm} = 1 \text{ μg/mL} = 1 \text{ mg/L} = 1 \text{ g/m}^3 \qquad (10)$$

and $$1 \text{ ppm} = 1000 \text{ ppb} \qquad (11)$$

In principle, this measurement of ozone is absolute and requires no external calibration. However, non-linearity of the photodiode response and electronics and other factors can result in a small measurement error of up to a few percent. Therefore, each instrument is calibrated against a reference dissolved ozone monitor that itself has been calibrated using a standard method such as the indigo method, providing calibration factors usually expressed as an offset and slope (gain or sensitivity).

Figure 4:
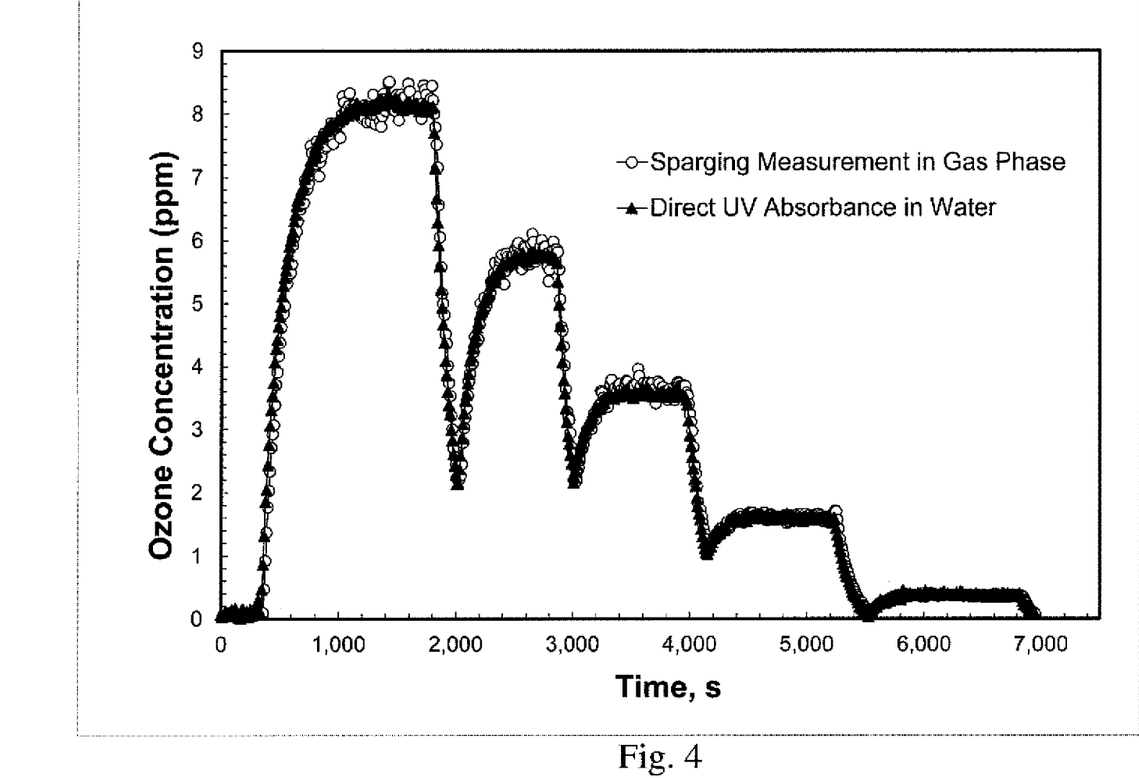
FIG. 4 is a comparison of simultaneous measurements made of dissolved ozone in water by a direct UV absorbance instrument (Direct UV Absorbance in Water) and by the present invention (Sparging Measurement in Gas Phase).

FIG. 4 is a comparison of the measured dissolved ozone concentrations vs time for sampling water containing dissolved ozone in water through a UV absorbance instrument (UV in Water) and into the present invention (MicroSparge). The measured ozone concentrations in ppm are compared over a time period of 50 minutes. These results demonstrate good agreement between the two instrumental methods.

EXAMPLE

Dissolved ozone in water was produced in an apparatus manufactured by Ozone Solutions, Inc. (Hull, Iowa) by continuous injection of ozone produced by corona discharge in oxygen into a circulating stream of water. Water was continuously sampled from the pressurized apparatus though a BMT (BMT Messtechnik GmbH, Berlin, Germany) Model 964-AQ-R1 dissolved ozone sensor, which is based on UV absorbance within water, and into a Model UV-106-W Aqueous Ozone Monitor, which is an embodiment of the present invention, described by FIG. 2. Dissolved ozone concentrations for the Model UV-106-W Aqueous Ozone Monitor were calculated in the firmware in real time based on the measured sample loop volume, air flow rate and ozone concentration profiles obtained during the 5-s sparging cycles as discussed earlier. The followed calibration equation was applied to the raw data to produce the final result:

$$C_{corrected} = 0.963[C_{measured} - 0.056]$$

The ozone concentration was varied in the range of ~0.0-8.2 ppm in steps by varying the current through the corona discharge. The concentrations of ozone measured by direct UV absorbance, labelled "Direct UV Absorbance in Water," and by the present invention, labelled "Sparging Measurement in Gas Phase," are plotted as a function of time in seconds in FIG. 4. As can been in the figure, there is excellent agreement between the two measurements throughout the experiment. The sparging measurements show more noise but faster response time than the direct UV measurements due to less signal averaging.

While a number of exemplary aspects and embodiments have been discussed above, those of skill in the art will recognize certain modifications, permutations, additions and sub-combinations therefore. It is therefore intended that the following appended claims hereinafter introduced are interpreted to include all such modifications, permutations, additions and sub-combinations are within their true sprit and scope. Each apparatus embodiment described herein has numerous equivalents.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. Whenever a range is given in the specification, all intermediate ranges and subranges, as well as all individual values included in the ranges given are intended to be included in the disclosure. When a Markush group or other grouping is used herein, all individual members of the group and all combinations and subcombinations possible of the group are intended to be individually included in the disclosure.

In general the terms and phrases used herein have their art-recognized meaning, which can be found by reference to standard texts, journal references and contexts known to those skilled in the art. The above definitions are provided to clarify their specific use in the context of the invention.

CITED LITERATURE

Standard Methods Committee, "4500-O3 Ozone (Residual)," Standard Methods for the Examination of Water and Waste Water, 1997.

Bader, H. and Hoigne, J., "Determination of ozone in water by the indigo method," *Water Research* 15, 449-456 (1981).

Bognar, J. A. and Birks, J. W., "Miniaturized Ultraviolet Ozonesonde for Atmospheric Measurements," *Analytical Chemistry* 68, 3059-3062 (1996).

Majewski, J., "Methods for measuring ozone concentration in ozone-treated water," Przegląd Elektrotechniczny (Electrical Review), ISSN 0033-2097, 88:9b (2012).

Wilson, K. L. and Birks, J. W. "Mechanism and Elimination of a Water Vapor Interference in the Measurement of Ozone by UV Absorbance," *Environmental Science and Technology* 40, 6361-6367 (2006)."

The invention claimed is:

1. A method to measure the concentration of dissolved ozone in pure or contaminated water comprising the steps of:
   a) capturing and isolating a known volume or mass of water to be analyzed;
   b) sparging the water sample with air or another unreactive gas at a known or measured flow rate for a period of time long enough to remove more than 60%, of the dissolved ozone,
   c) measuring the concentration of ozone in the sparging gas as a function of time,
   d) measuring or knowing the flow rate of the sparging gas as a function of time,
   e) mathematically integrating the product of the ozone concentration and gas flow rate over the sparging time interval to obtain the mass of ozone sparged from the sample,
   f) correcting for the fraction of ozone not sparged from the sample based on either calibration or integration under the measured exponential ozone decay curve to infinity, and
   g) calculating the dissolved ozone concentration in the original sample by dividing the corrected mass of ozone by the mass of the water sample and converting to appropriate units such as parts-per-million (ppm).

2. The method of claim 1 where the sparging gas is nitrogen, oxygen, helium or argon.

3. The method of claim 1 where the sparging time is 10 seconds or less.

4. The method of claim 1 where the ozone concentration is measured by UV absorbance.

5. The method of claim 1 where a calibration factor is applied based on separate measurements of dissolved ozone concentrations determined by a reference method.

6. The method of claim 1 where 75% or more of the ozone is sparged from the water sample.

7. The method of claim 1 where the water contains dissolved compounds that could interfere in the direct measurement of ozone by UV absorbance in water.

8. The method of claim 1 where the water contains particulate matter that could interfere in the direct measurement of ozone by UV absorbance in water.

9. The method of claim 1 where the water contains a strong acid or corrosive chemical.

10. The method of claim 1 where the water is undergoing treatment with ozone to become municipal drinking water, bottled water or other potable water.

11. The method of claim 1 where the water is ground water undergoing remediation for chemical contamination.

12. The method of claim 1 where the water contains dissolved ozone for the purpose of sanitizing food or sterilizing medical instruments.

13. The method of claim 1 where the water being analyzed contains dissolved ozone for the purpose of treatment for aquaculture.

* * * * *